US005750122A

United States Patent [19]

Evans et al.

[11] Patent Number: 5,750,122
[45] Date of Patent: May 12, 1998

[54] COMPOSITIONS FOR TREATING HAIR OR SKIN

[75] Inventors: Joel Franklin Evans, Cincinnati, Ohio; Bruce Russell Cox, Kobe, Japan; Michael Thomas Dodd, Edgewood, Ky.; Jeffrey Jon Hopkins, West Chester, Ohio

[73] Assignee: The Procter & Gamble Company, Cincinnati, Ohio

[21] Appl. No.: 629,256

[22] Filed: Apr. 8, 1996

Related U.S. Application Data

[63] Continuation-in-part of Ser. No. 587,162, Jan. 16, 1996, abandoned.

[51] Int. Cl.$^6$ ............................. A61K 7/48; A61K 7/06
[52] U.S. Cl. ..................... 424/401; 424/49; 424/59; 424/70.1; 424/70.12; 424/70.17; 514/844; 514/846; 514/859; 514/937; 514/941
[58] Field of Search .................... 424/401, 70.1, 424/70.12, 70.17, 59, 47; 514/844, 846, 859, 937, 941

[56] References Cited

U.S. PATENT DOCUMENTS

| 4,488,564 | 12/1984 | Grollier | 132/7 |
|---|---|---|---|
| 4,493,824 | 1/1985 | Abe | 424/70 |
| 4,705,681 | 11/1987 | Maes et al. | 424/70 |
| 4,863,725 | 9/1989 | Deckner et al. | 424/81 |
| 4,900,545 | 2/1990 | Wisotzki et al. | 424/70 |
| 4,938,960 | 7/1990 | Ismail | 424/195.1 |
| 5,100,660 | 3/1992 | Hawe et al. | 424/78.35 |
| 5,136,093 | 8/1992 | Smith | 564/197 |
| 5,139,772 | 8/1992 | Morita et al. | 424/70 |
| 5,211,941 | 5/1993 | Komori et al. | 424/70 |
| 5,332,569 | 7/1994 | Wood et al. | 424/70 |
| 5,342,611 | 8/1994 | Komori et al. | 424/70 |
| 5,362,484 | 11/1994 | Wood et al. | 424/70 |
| 5,541,220 | 7/1996 | Ismail | 514/458 |

FOREIGN PATENT DOCUMENTS

| 9462606 | 9/1994 | Australia . |
| 0 095 615 A | 12/1983 | European Pat. Off. . |
| 0 473 349 B1 | 3/1992 | European Pat. Off. . |
| 0 515 270 A2 | 11/1992 | European Pat. Off. . |
| 0 535 367 A2 | 4/1993 | European Pat. Off. . |
| 57149213 | 9/1982 | Japan . |
| 6126001 | 11/1986 | Japan . |
| 04230614 | 8/1992 | Japan . |
| 8608856 | 12/1986 | Spain . |
| 94/02148 A | 2/1994 | WIPO . |
| 94/14404 | 7/1994 | WIPO . |

OTHER PUBLICATIONS

Weiser et al. "Acceleration of Superficial Wound Healing by Panthenoln Zinc Oxide," Cosmetics & Toiletries, vol. 103, pp. 79–84, Oct. 1988.

*Primary Examiner*—Jyothsan Venkat
*Attorney, Agent, or Firm*—Loretta J. Henderson; David K. Dabbiere

[57] ABSTRACT

The present invention relates to compositions useful for treating hair or skin. These compositions comprise a topical vehicle containing panthenol and a polyalkyleneglycol having from 3 to about 12 repeating ethyleneglycol or propyleneglycol units.

19 Claims, No Drawings

COMPOSITIONS FOR TREATING HAIR OR SKIN

This application is a continuation-in-part of patent application Ser. No. 08/587,162, filed Jan. 16, 1996, and now abandoned.

TECHNICAL FIELD

The present invention relates to compositions useful for treating hair or skin. Specifically, these compositions are useful for delivering panthenol, and especially D-panthenol, to the hair or skin. These compositions comprise panthenol, a polyalkyleneglycol having from 3 to about 12 repeating ethyleneglycol or propyleneglycol units, and a topical vehicle. These compositions are useful as hair and skin conditioners.

BACKGROUND OF THE INVENTION

There exists a general need to provide compositions which are useful for treating the hair and skin to provide, for example, conditioning benefits. Both hair and skin are related keratinous substances and are constantly subjected to environmental stresses such as low humidity, UV radiation, contact with surfactants, and physical abrasion, and also to internal stresses which are a consequence of the natural aging process. Because of these stresses, the hair and the skin tend to loose their natural conditioning and moisturizing components and often appear rough, dry, and damaged. Regarding the hair, it is often difficult to keep the hair from tangling after it is washed and to prevent the occurrence of frizziness, split ends, and other undesirable effects. Regarding the skin, it is often difficult to keep the skin looking and feeling smooth, supple, and moisturized. Consequently, over the years, a wide variety of materials have been used in an attempt to treat the hair and skin. However, many conventional hair and skin conditioning materials have drawbacks such as not being effective or long-lasting, of being difficult to formulate, or of having negative aesthetic qualities.

Panthenol is a material that has been used to treat both the hair and skin. Panthenol is the alcohol form of vitamin $B_3$, which is also known as pantothenic acid. For example, U.S. Pat. No. 4,705,681, to Maes et al., issued Nov. 10, 1987, discloses hair treatment compositions containing the combination of one part by weight of D-panthenol to nine parts by weight of D-panthenol ethyl ether. Compositions for providing superficial wound healing containing the combination of panthenol and zinc oxide are disclosed in H. Weise et al., "Acceleration of Superficial wound Healing by Panthenol Zinc Oxide."*Cosmetics and Toiletries*, vol. 103, pp. 79–84, October 1988.

The benefits that can be obtained from using panthenol in hair and skin care compositions, however, are not fully realized because panthenol is a relatively expensive ingredient that is difficult to formulate and deliver from a finished product composition. Therefore, a need exists for developing formulation systems for efficiently and effectively delivering panthenol to the hair and skin.

It has surprisingly been found in the present invention that the combination of panthenol and certain low molecular weight polyalkylene glycols, i.e., polyethylene glycols or polypropylene glycols having from 3 to about 12 ethylene glycol or propylene glycol units, provides a highly effective and efficient, yet relatively economical system, for delivering panthenol to the hair or skin. It has been found that this combination of panthenol and polyalkylene glycol can be delivered in a wide variety of nonlimiting product forms including hair conditioners, shampoos, mousses, gels, tonics, skin lotions, skin creams, and skin cleanser.

It is therefore an object of the present invention to provide compositions for the treatment of hair or skin.

It is another object of the present invention to provide compositions containing panthenol in combination with a polyethyleneglycol or polypropylene glycol having from 3 to about 12 ethylene glycol or propylene glycol units.

It is another object of the present invention to provide compositions which are useful for conditioning the hair or skin.

It is another object of the present invention to provide methods for treating hair or skin.

These and other objects of this invention will become apparent in light of the following disclosure.

SUMMARY OF THE INVENTION

The present invention relates to a composition useful for application to the hair or skin comprising:

(a). a safe and effective amount of panthenol, (b). at least one polyalkylene glycol corresponding to the structure

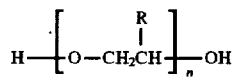

wherein R is selected from the group consisting of H, $CH_3$, and mixtures thereof, and n is an integer from 3 to about 12, and (c). a topical vehicle, wherein the weight ratio of said polyalkylene glycol to panthenol is from about 40:1 to about 1:40.

The present invention also relates to methods for treating hair or skin with these compositions.

All percentages and ratios used herein arc by weight of the total composition and all measurements made are at 25° C. or ambient room temperature, unless otherwise designated. All weight percentages, unless otherwise indicated, are on an actives weight basis. The invention hereof can comprise, consist of, or consist essentially of, the essential as well as optional ingredients and components described herein.

DETAILED DESCRIPTION OF THE INVENTION

It has been found in the present invention that the combination of panthenol and certain low molecular weight polyalkylene glycols, i.e., polyethylene glycols or polypropylene glycols having from 3 to about 12 ethylene glycol or propylene glycol units provides compositions that are useful for treating the hair or skin. These compositions are highly effective and efficient for delivering panthenol to the hair or skin. These compositions can be formulated in a wide variety of product forms including hair conditioners, shampoos, mousses, gels, tonics, skin lotions, skin creams, skin cleaners, and the like.

The term "topical application," as used herein, means to apply or spread the compositions of the present invention to the hair or to the surface of the skin.

The term "leave-on," as used herein, means a composition that is intended to be applied to and left on the hair or skin.

The term "rinse-off," as used herein, means a composition that is applied to the hair or skin and is subsequently rinsed from the hair or skin.

The term "wipe-off," as used herein, means a composition that is applied to the hair or skin and is subsequently wiped from the hair or skin.

The term "safe and effective amount," as used herein means an amount of the composition or components thereof sufficient to provide the desired benefit without causing undesired side effects or reactions.

The terms "cosmetically-acceptable" and "pharmaceutically-acceptable," as used herein, means that the compositions or components so described are of sufficiently high purity and are suitable for use in contact with human hair or skin without undue toxicity, incompatibility, instability, allergic response, and the like.

Panthenol

The compositions of the present invention comprise panthenol. The compositions should comprise a safe and effective amount of panthenol. The compositions typically comprise from about 0.001% to about 1%, preferably from about 0.005% to about 0.5%, and more preferably from about 0.01% to about 0.25%, by weight of the total composition of panthenol.

Panthenol is the alcohol corresponding to pantothenic acid, the acid being a member of the B complex vitamins. Panthenol is also known as pantothenol and 2,4-dihydroxy-N-(3-hydroxypropyl)-3,3-dimethylbutanamide. The material can exist as stereoisomers, e.g., the D(+) form, the L(−) form, the racemate, and other mixtures of the D(+) and L(−) forms. The D(+) form, which is also known as dexpanthenol or D-panthenol, is related to the naturally occurring form of pantothenic acid. Without being limited by theory, it is believed that the D(+) form of panthenol is the active material that is useful for treating the hair or hair. In preferred embodiments, the compositions of the present invention comprise D(+) panthenol (hereinafter designated simply as "D-panthenol").

Polyalkylene Glycol

The compositions of the present invention comprise at least one polyalkylene glycol. The compositions typically comprise from about 0.01% to about 20%, preferably from about 0.05% to about 10%, and more preferably from about 0.1% to about 5%, by weight of the total composition of at least one polyalkylene glycol.

The polyalkylene glycols useful herein are those corresponding to the following formula:

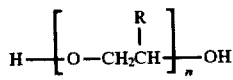

In the preceding formula, R is selected from the group consisting of H, CH$_3$, and mixtures thereof, preferably R is H. When R is H, the polyalkylene glycol is a polyethylene glycol, i.e. the polyalkylene glycol is composed of repeating units that are derived from ethylene glycol or ethylene oxide. When R is CH$_3$, the polyalkylene glycol is a polypropylene glycol, i.e. the polypropylene glycol is composed of repeating units that are derived from propylene glycol or propylene oxide. In the preceding formula n is an integer from 3 to about 12, preferably from about 4 to about 8, and more preferably about 4. Without being limited by theory, it is believed that the polyethylene glycol helps to plasticize or soften the hair or skin and thereby aid in the delivery and penetration of the panthenol. It has been found that polyalkylene glycols having an n value of 2 are not useful for preparing compositions of the present invention.

In the present invention the following nomenclature is used to designate a polyalkylene glycol. For example, a polyethylene glycol in which n is 4 is designated "polyethylene glycol 4." A polyethylene glycol in which n is 6 is designated "polyethylene glycol 6." Similar nomenclature is used for the polypropylene glycols.

Weight Ratio of Polyalkylene Glycol to Panthenol

In the compositions of the present invention the weight ratio of the polyalkylene glycol to the panthenol is from about 40:1 to about 1:40, preferably from about 20:1 to about 1:20, more preferably from about 10:1 to about 1:10, and most preferably from about 10:1 to about 1:1.

Topical Vehicle

The compositions of the present invention also comprise from about 50 to about 99.989%, preferably from about 75% to about 99.9%, and more preferably from about 80% to about 99% of a topical vehicle. The term "topical vehicle", as used herein, is well-known to one of ordinary skill in the art, and means one or more liquid or solid diluents, solvents, or carriers which are suitable for application to hair or skin and which are compatible with the panthenol, the polyalkylene, and any other components which can be present in the compositions. The term "compatible," as used herein, means that the topical vehicle is suitable for being commingled with the components of the present invention, and with each other, in a manner such that there is no interaction which would substantially reduce the utility or efficacy of the compositions under ordinary use situations. The topical vehicle must be a cosmetically acceptable or pharmaceutically acceptable carrier.

The topical compositions useful in the subject invention can be made into a wide variety of product types. These include, but are not limited to, leave-on hair conditioners, rinse-off hair conditioners, shampoos, hair mousses, hair sprays, hair tonics, hair gels, skin lotions, skin creams, skin gels, skin mousses, antiperspirant sprays and sticks, skin ointments, soaps, shower gels, powders, and a wide variety of cosmetics, i.e. lipsticks, foundations, eye shadows, make-ups, and the like. These product types can comprise several types of carrier systems including, but not limited to solutions, emulsions, gels, solids, and liposomes. Also useful are cleansing compositions which also deliver the components of the present invention to the skin during the cleansing process.

The topical compositions useful in the subject invention formulated as solutions typically include a pharmaceutically-acceptable aqueous or organic solvent. Water is a preferred solvent. Nonlimiting examples of suitable organic solvents include: ethanol, propylene glycol, glycerol, 1,2,4-butanetriol, sorbitol esters, 1,2,6-hexanetriol, isopropanol, sorbitol esters, butanediol, and mixtures thereof.

If the topical compositions useful in the subject invention are formulated as an aerosol and applied to the hair or skin as a spray-on, a propellant is added to a solution composition. Examples include chloro-fluorinated lower molecular weight hydrocarbons. A more complete disclosure of propellants useful herein can be found in Sagarin, *Cosmetics Science and Technology*, 2nd Edition, Vol. 2, pp. 443–465 (1972), which is incorporated herein by reference in its entirety.

If the compositions are formulated as an emulsion, preferably from about 0.1% to about 10%, more preferably from about 0.5% to about 2%, of the vehicle comprises an emulsifier. Emulsifiers can be nonionic, anionic or cationic. Suitable emulsifiers are disclosed in, for example, U.S. Pat. No. 3,755,560, issued Aug. 28, 1973, Dickert et al.; U.S. Pat. No. 4,421,769, issued Dec. 20, 1983, Dixon et al.; and McCutcheon's *Detergents and Emulsifiers*, North American Edition, pages 317–324 (1986), all of these references being incorporated herein by reference in their entirety. Various emulsion topical carriers, as well as other topical carriers, are also described in U.S. Pat. No. 5,306,485, to Robinson et al., issued Apr. 26, 1994, which is incorporated by reference herein in its entirety. The emulsions can be made in a variety of forms including water-in-oil, oil-in-water, silicone-in-water, and water-in-oil-in-water emulsions.

The compositions useful in the subject invention can be made in the form of cleansing compositions, in which case the compositions preferably would comprise from about 1% to about 50%, more preferably from about 5% to about 10%, of a surfactant.

ADDITIONAL COMPONENTS

A wide variety of additional components can be employed in he topical compositions herein. Non-limiting examples include the following:

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. The preferred carboxylic acid polymers are of two general types. The first type of polymer is a crosslinked homopolymer of an acrylic acid monomer or derivative thereof (e.g., wherein the acrylic acid has substituents on the two and three carbon positions independently selected from the group consisting of $C_{1-4}$ alkyl, —CN, —COOH, and mixtures thereof). The second type of polymer is a crosslinked copolymer having a first monomer selected from the group consisting of an acrylic acid monomer or derivative thereof (as just described in the previous sentence), a short chain alcohol (i.e., a $C_{1-4}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof), and mixtures thereof; and a second monomer which is a long chain alcohol (i.e. $C_{8-40}$) acrylate ester monomer or derivative thereof (e.g., wherein the acrylic acid portion of the ester has substituents on the two and three carbon positions independently selected from the group consisting of $C_{1-4}$ alkyl, —CN, —COOH, and mixtures thereof). Combinations of these two types of polymers are also useful herein.

In the first type of crosslinked homopolymers, the monomers are preferably selected from the group consisting of acrylic acid, methacrylic acid, ethacrylic acid, and mixtures thereof, with acrylic acid being most preferred. In the second type of crosslinked copolymers the acrylic acid monomer or derivative thereof is preferably selected from the group consisting of acrylic acid, methacrylic acid, ethacrylic acid, and mixtures thereof, with acrylic acid, methacrylic acid, and mixtures thereof being most preferred. The short chain alcohol acrylate ester monomer or derivative thereof is preferably selected from the group consisting of $C_{1-4}$ alcohol acrylate esters, $C_{1-4}$ alcohol methacrylate esters, $C_{1-4}$ alcohol ethacrylate esters, and mixtures thereof, with the $C_{1-4}$ alcohol acrylate esters, $C_{1-4}$ alcohol methacrylate esters, and mixtures thereof, being most preferred. The long chain alcohol acrylate ester monomer is selected from $C_{8-40}$ alkyl acrylate esters, with $C_{10-30}$ alkyl acrylate esters being preferred.

The crosslinking agent in both of these types of polymers is a polyalkenyl polyether of a polyhydric alcohol containing more than one alkenyl ether group per molecule, wherein the parent polyhydric alcohol contains at least 3 carbon atoms and at least 3 hydroxyl groups. Preferred crosslinkers are those selected from the group consisting of allyl ethers of sucrose and allyl ethers of pentaerythritol, and mixtures thereof. These polymers useful in the present invention are more fully described in U.S. Pat. No. 5,087,445, to Haffey et al., issued Feb. 11, 1992; U.S. Pat. No. 4,509,949, to Huang et al., issued Apr. 5, 1985; U.S. Pat. No. 2,798,053, to Brown, issued Jul. 2, 1957; which are both incorporated by reference herein in their entirety. See also, *CTFA International Cosmetic Ingredient Dictionary*, fourth edition, 1991, pp. 12 and 80; which are also incorporated herein by reference in their entirety.

Examples of commercially available homopolymers of the first type useful herein include the carbomers, which are homopolymers of acrylic acid crosslinked with allyl ethers of sucrose or pentaerytritol. The carbomers are available as the Carbopol® 900 series from B. F. Goodrich. Examples of commercially available copolymers of the second type useful herein include copolymers of $C_{10-30}$ alkyl acrylates with one or more monomers of acrylic acid, methacrylic acid, or one of their short chain (i.e. $C_{1-4}$ alcohol) esters, wherein the crosslinking agent is an allyl ether of sucrose or pentaerytritol. These copolymers are known as acrylates/C10–30 alkyl acrylate crosspolymers and are commercially available as Carbopol® 1342, Pemulen TR-1, and Pemulen TR-2, from B. F. Goodrich. In other words, examples of carboxylic acid polymer thickeners useful herein are those selected from the group consisting of carbomers, acrylates/C10–30 alkyl acrylate crosspolymers, and mixtures thereof.

Humectants and Moisturizers

The compositions of the present invention can also contain one or more humectants or moisturizers. A variety of these materials can be employed and each can be present at a level of from about 0.1% to about 20%, more preferably from about 0.5% to about 10%, and most preferably from about 1% to about 5%. These materials include guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); polyhydroxy alcohols such as sorbitol, glycerol, hexanetriol, propylene glycol, butylene glycol, hexylene glycol and the like; sugars and starches; sugar and starch derivatives (e.g., alkoxylated glucose); hyaluronic acid; lactamide monoethanolamine; acetamide monoethanolamine; and mixtures thereof. An especially preferred humectant or moisturizer material for use herein is glycerol.

Silicone Conditioning Agents

The compositions hereof can optionally include nonvolatile soluble or insoluble silicone conditioning agents or volatile silicone conditioning agents. By soluble what is meant is that the silicone conditioning agent is miscible with the topical vehicle so as to form part of the same phase. By insoluble what is meant is that the silicone forms a separate, discontinuous phase from the topical vehicle, such as in the form of an emulsion or a suspension of droplets of the silicone. The term "nonvolatile" as used herein shall mean that the silicone has a boiling point of at least about 260° C., preferably at least about 275° C., more preferably at least about 300° C. Such materials exhibit very low or no significant vapor pressure at ambient conditions. The term volatile shall mean that the silicone has a boiling point of from about 99° C. to about 260° C.

The silicone conditioning agent can be used in the compositions of the present invention at levels of from about .05% to about 10% by weight of the composition, preferably from about 0.1% to about 6%, more preferably from about 0.5% to about 5%, most preferably from about 0.5% to about 3%.

Soluble silicones include silicone copolyols, such as dimethicone copolyols, e.g. polyether siloxane-modified polymers, such as polypropylene oxide, polyethylene oxide modified polydimethylsiloxane, wherein the level of ethylene and/or propylene oxide sufficient to allow solubility in the composition.

Preferred, however, are insoluble silicones. The insoluble silicone conditioning agent for use herein will preferably have viscosity of from about 1,000 to about 2,000,000 centistokes at 25° C., more preferably from about 10,000 to about 1,800,000, even more preferably from about 100,000 to about 1,500,000. The viscosity can be measured by means of a glass capillary viscometer as set forth in Dow Corning Corporate Test Method CTM0004, Jul. 20, 1970.

Suitable insoluble, nonvolatile silicone fluids include polyalkyl siloxanes, polyaryl siloxanes, polyalkylaryl siloxanes, polyether siloxane copolymers, and mixtures thereof. Other insoluble, nonvolatile silicone fluids having conditioning properties can also be used. The term "silicone fluid" shall mean flowable silicone materials having a viscosity of less than 1,000,000 centistokes at 25° C. Generally, the viscosity of the fluid will be between about 5 and 1,000,000 centistokes at 25° C., preferably between about 10 and about 300,000.

Silicone fluids hereof also include polyalkyl or polyaryl siloxanes with the following structure:

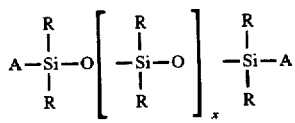

wherein R is alkyl or aryl, and x is an integer from about 7 to about 8,000 may be used. "A" represents groups which block the ends of the silicone chains.

The alkyl or aryl groups substituted on the siloxane chain (R) or at the ends of the siloxane chains (A) may have any structure as long as the resulting silicones remain fluid at room temperature, are hydrophobic, are neither irritating, toxic nor otherwise harmful when applied to the hair or skin, are compatible with the other components of the composition, are chemically stable under normal use and storage conditions, and are capable of being deposited on and of conditioning hair or skin.

Suitable A groups include methyl, methoxy, ethoxy, propoxy, and aryloxy. The two R groups on the silicone atom may represent the same group or different groups. Preferably, the two R groups represent the same group. Suitable R groups include methyl, ethyl, propyl, phenyl, methylphenyl and phenylmethyl. The preferred silicones are polydimethyl siloxane, polydiethylsiloxane, and polymethylphenylsiloxan. Polydimethylsiloxane is especially preferred.

The nonvolatile polyalkylsiloxane fluids that can be used include, for example, polydimethylsiloxanes. These siloxanes are available, for example, from the General Electric Company in their Viscasil R® and SF96® series, and from Dow Corning in their Dow Corning 200® series.

The polyalkylaryl siloxane fluids that can be used, also include, for example, polymethylphenylsiloxanes. These siloxanes are available, for example, from the General Electric Company as SF1075® methyl phenyl fluid or from Dow Corning as 556 Cosmetic Grade Fluid®.

The polyether siloxane copolymers that can be used include, for example, a polypropylene oxide modified polydimethylsiloxane (e.g., Dow Corning DC-1248®) although ethylene oxide or mixtures of ethylene oxide and propylene oxide may also be used.

References disclosing suitable silicone fluids include U.S. Pat. No. 2,826,551, Geen; U.S. Pat. No. 3,964,500, Drakoff, issued Jun 22, 1976; U.S. Pat. No. 4,364,837, Pader; and British Pat. No. 849,433, Woolston. All of these patents are incorporated herein by reference in their entirety.

Another silicone conditioning material that can be especially useful in the compositions is insoluble silicone gum. The term "silicone gum", as used herein, means polyorganosiloxane materials having a viscosity at 25° C. of greater than or equal to 1,000,000 centistokes. Silicone gums are described by Petrarch and others including U.S. Pat. No. 4,152,416, Spitzer et al., issued May 1, 1979 and Noll, Walter, Chemistry and Technology of Silicones, New York: Academic Press 1968. The "silicone gums" will typically have a mass molecular weight in excess of about 200,000, generally between about 200,000 and about 1,000,000. Specific examples include polydimethylsiloxane, (polydimethylsiloxane) (methylvinylsiloxane) copolymer, poly(dimethylsiloxane) (diphenyl siloxane) (methylvinylsiloxane) copolymer and mixtures thereof.

Preferably the silicone hair conditioning agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30, preferably from about 40:60 to about 60:40. The polydimethylsiloxane gum/ polydimethylsiloxane fluid can be used alone or in a suitable carrier such as polysorbate 80.

Also, a silicone resin can be included in the silicone conditioning agent. Silicone resins are highly crosslinked polymeric siloxane systems. The crossliking is introduced through the incorporation of trifunctional and tetrafunctional silanes with monofunctional or difunctional, or both, silanes during manufacture of the silicone resin. As is well understood in the art, the degree of crosslinking that is required in order to result in a silicone resin will vary according to the specific silane units incorporated into the silicone resin. In general, silicone materials which have a sufficient level of trifunctional and tetrafunctional siloxane monomer units (and hence, a sufficient level of crosslinking) such that they dry down to a rigid, or hard, film are considered to be silicone resins. The ratio of oxygen atoms to silicon atoms is indicative of the level of crosslinking in a particular silicone material. Silicone materials which have at least about 1.1 oxygen atoms per silicon atom will generally be silicone resins herein. Preferably, the ratio of oxygen:silicon atoms is at least about 1.2:1.0. Silanes used in the manufacture of silicone resins include monomethyl-, dimethyl-, trimethyl-, monophenyl-, diphenyl-, methylphenyl-, monovinyl-, and methylvinyl-chlorosilanes, and tetrachlorosilane, with the methyl-substituted silanes being most commonly utilized. Preferred resins are offered by General Electric as GE SS4230® and SS4267®. Commercially available silicone resins will generally be supplied in a dissolved form in a low viscosity volatile or nonvolatile silicone fluid. The silicone resins for use herein should be supplied and incorporated into the present compositions in such dissolved form, as will be readily apparent to those skilled in the art.

Another optional silicone conditioning agent is a volatile silicone solvent. The volatile silicone allows for easier and more even dispersion of silicone gums and resins in the compositions. The silicones can be either cyclic or linear polydimethyl siloxanes. The number of silicon atoms in the cyclic silicones is from about 3 to about 7, most preferably 4 or 5. These materials are also known as cyclomethicones. Linear polydimethyl siloxanes useful in the present invention generally contain from about 3 to about 9 silicon atoms and have the general formula:

$(CH_3)_3Si-O-[Si(CH_3)_2O]_m-Si(CH_3)_3$ wherein m=1–7.

Volatile silicone solvents of the above described types are widely available, e.g. from Dow Corning as 344, 345 and 200 Fluids®; Union Carbide as Silicone 7202 and 7158®; and Stauffer Chemical as SWS-03314®.

Background material on silicones including sections discussing silicone fluids, gums, and resins, as well as manufacture of silicones, can be found in Encyclopedia of Polymer Science and Engineering, Volume 15, Second Edition, pp 204–308, John Wiley & Sons, Inc., 1989, incorporated herein by reference.

Other Additional Components

The compositions of the present invention can comprise a wide range of additional components. The *CTFA Cosmetic Ingredient Handbook*, Second Edition, 1992, which is incorporated by reference herein in its entirety, describes a wide variety of nonlimiting cosmetic and pharmaceutical ingredients commonly used in the hair or skin care industry, which are suitable for use in the compositions of the present invention. Nonlimiting examples of functional classes of ingredients are described at page 537 of this reference. Examples of these functional classes include: absorbents, abrasives, anti-acne agents, anticaking agents, antifoaming agents, antimicrobial agents, antioxidants, binders, biological additives, buffering agents, bulking agents, chelating agents, chemical additives, colorants, cosmetic astringents, cosmetic biocides, denaturants, drug astringents, external analgesics, film formers, fragrance components, humectants, opacifying agents, pH adjusters, plasticizers, preservatives, propellants, reducing agents, skin bleaching agents, skin-conditioning agents (emollient, humectants, miscellaneous, and occlusive), skin protectants, solvents, surfactants (cleansing agents, emulsifying agents, foam boosters, hydrotropes, solubilizing agents, and suspending agents), suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include emulsifiers, solubilizing agents, sequestrants, and keratolytics, and the like.

Nonlimiting examples of these additional components cited in the *CTFA Cosmetic Ingredient Handbook*, as well as other materials useful herein, include the following: vitamins and derivatives thereof [e.g., vitamin C, Vitamin A (i.e. retinoic acid), retinol, retinoids, and the like]; sunscreening agents (nonlimiting examples of sunscreening agents are disclosed in U.S. Pat. No. 5,219,558, to Woodin, Jr. et al., issued Jun. 15, 1993, which is incorporated herein by reference in its entirety); anti-oxidants; anti-microbial agents; preservatives; emulsifiers; polymers for aiding the film-forming properties and substantivity of the composition (such as a copolymer of eicosene and vinyl pyrrolidone, an example of which is available from GAF Chemical Corporation as Ganex® V-220); preservatives for maintaining the antimicrobial integrity of the compositions; anti-acne medicaments (e.g., benzoyl peroxide, resorcinol, sulfur, salicylic acid, erythromycin, zinc, and the like); skin bleaching (or lightening) agents including but not limited to hydroquinone, kojic acid; antioxidants; chelators and sequestrants; crosslinked and noncrosslinked nonionic and cationic polyacrylamides [e.g., Salcare SC92 which has the CTFA designation polyquaternium 32 (and) mineral oil, Salcare SC95 which has the CTFA designation polyquaternium 37 (and) mineral oil (and) PPG-1 trideceth-6, and Salcare SC96 which has the CTFA designation polyquaternium 37 (and) dicaprylate/dicaprate (and) PPG-1 trideceth-6, and the nonionic Seppi-Gel polyacrylamides available from Seppic Corp.]; aesthetic components such as fragrances, pigments, colorings, essential oils, skin senates, astringents, skin soothing agents, skin healing agents and the like, [nonlimiting examples of these aesthetic components include clove oil, menthol, camphor, eucalyptus oil, eugenol, menthyl lactate, witch hazel distillate, bisabolol, dipotassium glycyrrhizinate and the like]; and skin conditioning agents such as urea and glycerol, and also the propoxylated glycerols described in U.S. Pat. No. 4,976,953, to Orr et al., issued Dec. 11, 1990, which is incorporated by reference herein in its entirety. Also useful optional components are panthenol derivatives such as pantothenic acid, pantetheine, pantethine, C1–C30 alkyl esters of pantothenic acid, C1–C30 carboxylic acid esters of panthenol, C1–C30 alkyl ethers of panthenol, and mixtures thereof.

Methods of Treating Hair or Skin

The compositions of the present invention are useful for treating the hair or skin in humans and other biological subjects.

The compositions of the present invention are administered topically to a biological subject, i.e., by the direct laying on or spreading of the composition on the hair or skin. The composition can be in the form of a leave-on product which is applied and left on as in the case of a non-rinse hair conditioner, hair spray, mousse, or skin cream or lotion. In other embodiments the composition can be applied and removed by rinsing or wiping as in the case of a rinse-off or wipe-off products such as a hair rinse conditioner, shampoo, or skin cleanser.

A wide range of quantities of the compositions of the present invention can be employed to deliver the panthenol to the hair or skin. Quantities of the compositions will vary with the product form and intended use. Typical amounts used can range from about 0.1 mg/cm$^2$ to about 25 mg/cm$^2$ of surface area of skin or of scalp.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

Ingredients are identified by chemical or CTFA name.

Examples 1–4

Hair Grooming Tonics

The following hair grooming tonics are prepared by combining the following ingredients using conventional mixing techniques.

| Component (wt %) | 1 | 2 | 3 | 4 |
|---|---|---|---|---|
| Water | QS 100 | QS 100 | QS 100 | QS 100 |
| Polyethylene Glycol 4 | 0.10 | 0.40 | 2.5 | 5.0 |
| D-Panthenol | 0.01 | 0.01 | 0.25 | 0.5 |
| Ethanol | 20 | 20 | 20 | 20 |
| Fragrance | 0.10 | 0.10 | 0.10 | 0.10 |

The resulting compositions are useful grooming the hair and for delivering D-panthenol to the hair.

Examples 5–8

Hair Grooming Tonics

The following hair grooming tonics are prepared by combining the following ingredients using conventional mixing techniques.

| Component (wt %) | 5 | 6 | 7 | 8 |
|---|---|---|---|---|
| Water | QS 100 | QS 100 | QS 100 | QS 100 |
| Salcare ® SC96 (1) | 0.00 | 1.00 | 1.00 | 0.00 |
| Salcare ® SC95 (2) | 0.50 | 0.00 | 0.00 | 2.00 |
| Silicone Emulsion (3) | 0.00 | 1.00 | 2.00 | 0.50 |
| Polyethylene Glycol 4 | 0.45 | 0.45 | 0.45 | 0.225 |
| D-Panthenol | 0.05 | 0.05 | 0.05 | 0.025 |
| Fragrance | 0.10 | 0.10 | 0.10 | 0.10 |
| Disodium EDTA | 0.15 | 1.50 | 0.15 | 0.15 |
| Ethanol | 0.00 | 98.05 | 70.00 | 0.00 |

(1) Polyquaternium 37 (and) Propylene Glycol Dicaprylate/Dicaprate (and) PPG-1 Trideceth 6, commercially available from Allied Colloids Ltd., (Norfolk, VA, USA).
(2) Polyquaternium 37 (and) Mineral Oil (and) PPG-1 Trideceth 6, commercially available from Allied Colloids Ltd., (Norfolk, VA, USA).
(3) Mixture of polydimethylsiloxane gum/polydimethylsiloxane fluid and polysorbate 80.

The resulting compositions are useful for grooming the hair and delivering D-panthenol to the hair.

Examples 9–13

Non-aerosol Hair Sprays

The following non-aerosol hair sprays are prepared by combining the following ingredients using conventional mixing techniques.

| Component (wt %) | 9 | 10 | 11 | 12 | 13 |
|---|---|---|---|---|---|
| Water | QS 100 | QS 100 | QS 100 | QS 100 | QS 100 |
| Salcare ® SC96[1] | 1.00 | 0.00 | 0.70 | 2.00 | 1.00 |
| Salcare ® SC95[2] | 0.00 | 1.00 | 0.00 | 0.00 | 0.00 |
| Silicone Emulsion[3] | 0.00 | 1.00 | 1.00 | 2.00 | 0.60 |
| PVPNA Copolymer[4] | 0.00 | 1.00 | 0.00 | 2.00 | 1.00 |
| Polyethylene Glycol 4 | 0.50 | 0.50 | 2.00 | 0.50 | 0.45 |
| Polyethylene Glycol 5000 | 0.005 | 0.01 | 0.00 | 0.10 | 0.01 |
| Disodium EDTA | 1.00 | 0.15 | 0.15 | 0.75 | 0.15 |
| Preservative | 0.35 | 0.35 | 0.35 | 0.35 | 0.35 |
| Fragrance | 1.00 | 1.00 | 1.00 | 1.00 | 0.05 |
| Ethanol | 70.00 | 0.00 | 0.00 | 0.00 | 0.00 |
| D-Panthenol | 0.05 | 0.02 | 1.00 | 0.02 | 0.05 |
| Crotein Q | 0.00 | 0.00 | 0.02 | 0.00 | 0.01 |
| Panthenyl-Ethyl-Ether | 0.02 | 0.25 | 0.00 | 0.25 | 0.01 |
| OMC | 0.00 | 0.00 | 0.00 | 0.00 | 0.01 |
| Silk Amino Acids | 0.00 | 0.02 | 0.00 | 0.00 | 0.01 |

[1] Polyquaternium 37 (and) Propylene Glycol Dicaprylate/Dicaprate (and) PPG-1 Trideceth 6, commercially available from Allied Colloids Ltd., (Norfolk, VA, USA).
[2] Polyquaternium 37 (and) Mineral Oil (and) PPG-1 Trideceth 6, commercially available from Allied Colloids Ltd., (Norfolk, VA, USA).
[3] Mixture of polydimethylsiloxane gum/polydimethylsiloxane fluid and polysorbate 80.
[4] Polyvinylpyrollidone/Vinyl acetate (70/30) available from ISP 1. Polyquaternium 37 (and) Propylene Glycol Dicaprylate/ Dicaprate (and) PPG-1 Trideceth 6, commercially available from Allied Colloids Ltd., (Norfolk, Va. USA).
2. Polyquaternium 37 (and) Mineral Oil (and) PPG-1 Trideceth 6, commercially available from Allied Colloids Ltd., (Norfolk, Va. USA).
3. Mixture of polydimethylsiloxane gum/ polydimethylsiloxane fluid and polysorbate 80.
4. Polyvinylpyrollidone/Vinyl acetate (70/30) available from ISP The resulting compositions are useful for spraying on the hair and for delivering D-panthenol to the hair.

Example 14–16

Non-aerosol Hair Sprays

The following non-aerosol hair spray compositions are prepared using conventional mixing techniques.

| Component (wt %) | 14 | 15 | 16 |
|---|---|---|---|
| Water | Qs 100 | QS 100 | QS 100 |
| Salcare ® SC96[1] 0.70 | 0.5 | 0.05 | |
| Ethanol | 79.00 | 79.0 | 86.40 |
| Silicone Emulsion[2] | 0.50 | 0.00 | 1.00 |
| Diisobutyl Adipate | 0.70 | 0.00 | 0.00 |
| Potassium Hydroxide (45% by weight aqueous solution) | 1.00 | 1.00 | 1.00 |
| Gantrez ES225[3] 8.00 | 8.00 | 8.00 | |
| Disodium EDTA 0.15 | 0.15 | 0.15 | |
| Perfume | 0.20 | 0.20 | 0.20 |

[1] Polyquaternium 37 (and) Propylene Glycol Dicaprylate/Dicaprate (and) PPG-1 Trideceth 6, commercially available from Allied Colloids Ltd., (Norfolk, VA, USA).
[2] Mixture of polydimethylsiloxane gum/polydimethylsiloxane fluid and polysorbate 80.
[3] Organic resin, poly(methylvinyl ether/maleic acid)monoethyl ester, commercially available as a 50% ethanol solution from ISP.

1. Polyquaternium 37 (and) Propylene Glycol Dicaprylate/ Dicaprate (and) PPG-1 Trideceth 6, commercially available from Allied Colloids Ltd., (Norfolk, Va. USA).
2. Mixture of polydimethylsiloxane gum/ polydimethylsiloxane fluid and polysorbate 80.
3. Organic resin, poly(methylvinyl ether/maleic acid) monoethyl ester, commercially available as a 50% ethanol solution from ISP.

This product is prepared by dissolving the Salcare® SC96 in the ethanol and mixing for several minutes until all of the premix is dissolved. Diisopropyl adipate is added if applicable. Potassium hydroxide is then added. Water or water/ surfactant, as applicable, is added. Fragrance is added last. All ingredients are added under mixing conditions. The product can be packaged in conventional nonaerosol pump spray containers and compressed air pump spray aerosol containers.

The resulting compositions are useful for spraying on the hair and delivering D-panthenol to the hair.

Examples 17–18

Mousses

The following hair mousse compositions are prepared using conventional mixing techniques.

Premix A

| Component (wt %) | 17 | 18 |
|---|---|---|
| Water | QS 100 | Qs 100 |
| Salcare SC96[1] | 0.54 | 2.15 |
| Silicone Emulsion[2] | 3.22 | 0.00 |
| Ethanol | 16.13 | 16.13 |
| Gaffix VC713[3] | 4.30 | 5.38 |
| Cocamine oxide | 0.65 | 0.65 |

-continued

| Component (wt %) | 17 | 18 |
|---|---|---|
| Cocamide DEA | 0.32 | 0.32 |
| Polyethylene Glycol 4 | 0.48 | 0.38 |
| Panthenol | 0.05 | 0.16 |
| Perfume | 0.11 | 0.11 |
| Total Premix | 100.00 | 100.00 |

Mousse

| | | |
|---|---|---|
| Premix A | 93.00 | 93.00 |
| Isobutane Propellant | 7.00 | 7.00 |
| | 100.00 | 100.00 |

1. Polyquaternium 37 (and) Propylene Glycol Dicaprylate/Dicaprate (and) PPG-1 Trideceth 6, commercially available from Allied Colloids Ltd., (Norfolk, Va. USA).
2. Mixture of polydimethylsiloxane gum/polydimethylsiloxane fluid and polysorbate 80.
3. Vinyl caprolactam/polyvinylpyrrolidone/dimethylaminoethyl methacrylate copolymer, commercially available from ISP.

The composition is made by blending all of the ingredients in Premix A at ambient temperature with mixing. Aluminum aerosol cans are then filled with 93 parts of the Premix A, affixed with a valve which is crimped into position, and pressure-filled with 7 parts isobutane.

The resulting compositions are useful for styling the hair and delivering D-panthenol to the hair.

Example 19

Aerosol Hair Spray

An aerosol hair spray composition of the present invention is prepared using conventional mixing techniques as follows:

Premix A

| Component (wt %) | 19 |
|---|---|
| Salcare SC96 (1) | 1.27 |
| Silicone Emulsion (2) | 2.53 |
| Water | 3.80 |
| Polyethylene Glycol 4 | 0.48 |
| Panthenol | 0.15 |
| Ethanol | QS 100 |
| GantrezES225 (3) | 10.13 |
| DisodiumEDTA | 0.19 |
| KOH (45% solution) | 1.27 |
| Hair Spray Premix | 100.00 |
| Hair Spray Premix | 79.00 |
| Isobutane Propellant | 15.00 |
| Difluoroethane Propellant | 6.00 |
| | 100.00 |

1. Polyquaternium 37 (and) Propylene Glycol Dicaprylate/Dicaprate (and) PPG-1 Trideceth 6, commercially available from Allied Colloids Ltd., (Norfolk, Va. USA).
2. Mixture of polydimethylsiloxane gum/polydimethylsiloxane fluid and polysorbate 80.
3. Organic resin, poly(methylvinyl ether/maleic acid) monoethyl ester, commercially available as a 50% ethanol solution from ISP.

All of the Premix A ingredients are mixed together at ambient temperature until the polymer is dissolved. The mixture is placed in an aerosol can which is then equipped with a conventional aerosol spray can valve which is vacuum crimped in place. The propellants are then filled through the valve and the can is equipped with a conventional aerosol spray can activator.

The resulting composition is useful for spraying the hair and delivering D-panthenol to the hair.

Example 20

Skin Lotion

A leave-on lotion composition is prepared by combining the following ingredients using conventional mixing techniques.

| Ingredients | Weight Percent |
|---|---|
| Phase A | |
| Water | QS 100 |
| Glycerin | 3.00 |
| Tetrasodium EDTA | 0.02 |
| Phase B | |
| PPG-15 Stearyl Ether | 4.00 |
| Stearyl Alcohol | 0.75 |
| Polyethylene Glycol 4 | 2.00 |
| D-Panthenol | 0.50 |
| Cetyl Alcohol | 0.75 |
| Steareth-21 | 0.45 |
| Steareth-2 | 0.05 |
| Dimethicone | 0.60 |
| Polyquaternium-37 (and) Mineral Oil (and) PPG-1 Trideceth-6 | 1.50 |
| Phase C | |
| Triethanolamine | 0.15 |
| Phase D | |
| Fragrance | 0.10 |
| Phase E | |
| Cetyl Dimethyl Betaine | 2.00 |
| Sodium Lauryl Sulfate | 1.00 |

In a suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next the fragrance is added with mixing. Next, the mixture is cooled to 35° C. In a separate vessel, the Phase E ingredients are combined and added to the remaining mixture with stirring.

The resulting lotion composition is useful for delivering D-panthenol to the skin.

Example 21

Anti-Acne Lotion

An anti-acne lotion is prepared by combining the following ingredients using conventional mixing techniques.

| Ingredients | Weight Percent |
|---|---|
| Phase A | |
| Water | QS 100 |
| Glycerin | 4.00 |
| Disodium EDTA | 0.10 |
| Carbomer | 0.60 |
| Acrylates/C10–30 Alkylacrylates Crosspolymer | 0.05 |
| Phase B | |
| Stearyl Alcohol | 2.25 |
| Cetyl Alcohol | 2.25 |

-continued

| Ingredients | Weight Percent |
| --- | --- |
| Steareth-100 | 0.50 |
| Distearyl Dimethyl Ammonium Chloride | 0.20 |
| Polyethylene Glycol 4 | 1.0 |
| D-Panthenol | 0.1 |
| Phase C | |
| Triethanolamine | 0.50 |
| Phase D | |
| Benzoyl Peroxide | 2.50 |
| Phase E | |
| Cetyl Dimethyl Betaine | 1.00 |
| Sodium Lauryl Sulfate | 0.50 |

In a suitable vessel, the Phase A ingredients are heated with stirring to about 75° C. In a separate vessel, the Phase B ingredients are heated with stirring to about 75° C. Phase B is then added to Phase A with mixing. Next Phase C is added with mixing. Next, the mixture is cooled to 35° C. Next the benzoyl peroxide is added with mixing. In a separate vessel, the Phase E ingredients are combined and added to the remaining mixture with stirring.

The resulting leave-on composition is useful for preventing and treating acne and for delivering D-panthenol to the skin.

Example 22

Sunscreen Composition

An oil-in-water emulsion is prepared by combining the following components utilizing conventional mixing techniques.

| Ingredients | Weight % |
| --- | --- |
| Phase A | |
| Water | QS 100 |
| Carbomer 954[1] | 0.24 |
| Carbomer 1342[2] | 0.16 |
| Disodium EDTA | 0.05 |
| Phase B | |
| Isoarachidyl Neopentanoate | 2.00 |
| PVP Eicosene Copolymer[3] | 2.00 |
| Octyl Methoxycinnamate | 7.50 |
| Octocrylene | 4.00 |
| Oxybenzone | 1.00 |
| Titanium Dioxide | 2.00 |
| Cetyl Palmitate | 0.75 |
| Stearoxytrimethylsilane (and) Stearyl Alcohol | 0.50 |
| Glyceryl Tribehenate | 0.75 |
| Dimethicone | 1.00 |
| Polyethylene Glycol 4 | 1.00 |
| D-Panthenol | 0.05 |
| DEA-Cetyl Phosphate | 0.20 |
| Phase C | |
| Water | 2.00 |
| Triethanolamine 99% | 0.60 |
| Phase D | |
| Water | 2.00 |
| Butylene Glycol | 2.00 |
| DMDM Hydantoin (and) Iodopropynyl Butylcarbamate[4] | 0.25 |
| dL Panthenol | 1.00 |

-continued

| Ingredients | Weight % |
| --- | --- |
| Phase E | |
| Cyclomethicone | 1.00 |

[1] Available as Carbopol® 954 from B. F. Goodrich.
[2] Available as Carbopol® 1342 from B. F. Goodrich.
[3] Available as Ganex V-220 from GAF Corporation.
[4] Available as Glydant Plus from Lonza.

In a suitable vessel the Phase A ingredients are dispersed in the water and heated to 75°–85° C. In a separate vessel the Phase B ingredients (exceptDEA-Cetyl Phosphate) are combined and heated to 85°–90° C. until melted. Next, the DEA-Cetyl Phosphate is added to the liquid Phase B and stirred until dissolved. This mixture is then added to Phase A to form the emulsion. The Phase C ingredients are combined until dissolved and then added to the emulsion. The emulsion is then cooled to 40°–45° C. with continued mixing. In another vessel, the Phase D ingredients are heated with mixing to 40°–45° C. until a clear solution is formed and this solution is then added to the emulsion. Finally, the emulsion is cooled to 35° C. and the Phase E ingredient is added and mixed.

This emulsion is useful for topical application to the skin to provide protection from the harmful effects of ultraviolet radiation and to deliver D-panthenol to the skin.

Example 23

Topical Analgesic Composition

A topical analgesic composition is made by combining the following ingredients utilizing conventional mixing techniques.

| Ingredient | Weight % |
| --- | --- |
| Water, Purified | QS 100 |
| Ibuprofen | 2.0 |
| Polyethylene Glycol 4 | 2.0 |
| D-Panthenol | 0.2 |
| Ethanol (SDA 40) | 20.0 |

The composition useful as a topical analgesic and for delivering D-panthenol to the skin

Example 24

Artificial Tanning Composition

A composition for sunless tanning is made by combining the following ingredients utilizing conventional mixing techniques.

| Ingredient | Weight % |
| --- | --- |
| Water | QS 100 |
| Carbomer 934[1] | 0.20 |
| Carbomer 980[2] | 0.15 |
| Acrylic Acid Copolymer[3] | 0.15 |
| Phase B | |
| PPG-20 Methyl Glucose Ether Distearate | 2.00 |
| Polyethylene Glycol 4 | 1.0 |
| Panthenol | 0.1 |
| Mineral Oil | 2.00 |
| Stearyl Alcohol | 1.00 |
| Shea Butter | 1.00 |
| Cetyl Alcohol | 1.00 |
| Ceteareth-20 | 2.50 |
| Ceteth-2 | 1.00 |

-continued

| Ingredient | Weight % |
|---|---|
| Ceteth-10 | 1.00 |
| Phase C | |
| DEA-Cetyl Phosphate | 0.75 |
| Phase D | |
| Dihydroxyacetone | 3.00 |
| Phase E | |
| Butylene Glycol | 2.00 |
| DMDM Hydantoin (and) Idodopropynyl Butylcarbamate | 0.25 |
| Phase F | |
| Fragrance | 1.00 |
| Cyclomethicone | 2.00 |

[1] Available as Carbopol® 934 from B. F. Goodrich.
[2] Available as Carbopol® 980 from B. F. Goodrich.
[3] Available as Pemulen TR1 from B. F. Goodrich.

In a suitable vessel the Phase A ingredients are dispersed in the water and heated to 75°–85° C. In a separate vessel the Phase B ingredients are combined and heated to 85°–90° C. until melted. Next, the DEA-Cetyl Phosphate is added to the liquid Phase B and stirred until dissolved. This mixture is then added to Phase A to form the emulsion. The emulsion is cooled to 40°–45° C. with continued mixing. Next, in a separate vessel, the dihydroxyacetone is dissolved in water and the resulting solution is mixed into the emulsion. In another vessel, the Phase E ingredients are heated with mixing to 40°–45° C. until a clear solution is formed and this solution is then added to the emulsion. Finally, the Phase F ingredients are added to the emulsion with mixing, which is then cooled to 30°–35° C., and then to room temperature.

This emulsion is useful for topical application to the skin to provide an artificial tan for delivering D-panthenol.

Alternatively, in the foregoing Examples 1–24, the polyethylene glycol 4 can be replaced with an equal weight of one of the other polyethylene glycols, i.e. polyethylene glycol 3, or polyethylene glycols 5 through 12, or polypropylene glycols, i.e. polypropylene glycols 3 through 12, as described herein.

What is claimed is:

1. A hair or skin composition comprising:
   (a) a safe and effective amount of panthenol.
   (b) at least one polyalkylene glycol corresponding to the structure

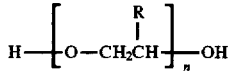

wherein R is selected from the group consisting of H, CH$_3$, and mixtures thereof, and n is an integer from 3 to about 8, and
   (c) a polyacrylamide selected from the group consisting of cross linked and noncrosslinked nonionic and cationic polyacrylamide
   (d) a silicone conditioning agent wherein the silicone agent comprises a mixture of a polydimethylsiloxane gum, having a viscosity greater than about 1,000,000 centistokes and polydimethylsiloxane fluid having a viscosity of from about 10 centistokes to about 100,000 centistokes, wherein the ratio of gum to fluid is from about 30:70 to about 70:30
   (e) a topical vehicle,
wherein the weight ratio of said polyalkylene glycol to panthenol is from about 10:1 to about 1:10.

2. A composition according to claim 1 wherein said panthenol is D-panthenol.

3. A composition according to claim 2 comprising from about 0.001% to about 1% of said D-panthenol, from about 0.01% to about 20% of said polyalkylene glycol, and from about 50% to about 99.989% of said topical vehicle.

4. A composition according to claim 2 wherein the weight ratio of said polyalkylene glycol to said D-panthenol is from about 10:1 to about 1:1.

5. A composition according to claim 1 wherein R is H.

6. A composition according to claim 5 wherein n is an integer from about 4 to about 8.

7. A composition according to claim 6 wherein n is about 4.

8. A composition according to claim 1 wherein said topical vehicle comprises water.

9. A composition according to claim 1 wherein said topical vehicle comprises ethanol.

10. A composition according to claim 1 wherein said topical vehicle is in the form of an oil-in-water emulsion.

11. A composition according to claim 1 wherein said topical vehicle is in the form of a water-in-oil emulsion.

12. A composition according to claim 1 wherein said topical vehicle is in the form of a silicone-in-water emulsion.

13. A method of treating hair comprising applying a safe and effective amount of the composition of claim 1 to the hair.

14. A method of treating hair comprising applying a safe and effective amount of the composition of claim 2 to the hair.

15. A method of treating hair comprising applying a safe and effective amount of the composition of claim 3 to the hair.

16. The composition of claim 1 comprising from about 0.01% to about 5% of said polyalkylene glycol and from about 0.001% to about 0.5% by weight of panthenol.

17. The composition of claim 16 comprising from about 0.1% to about 5% of said polyalkylene glycol and from about 0.01% to about 0.25% by weight of panthenol.

18. The composition of claim 16 wherein the weight ratio of said polyalkylene glycol to said panthenol is from about 10:1 to about 1:1.

19. The composition of claim 18 wherein said polyalkylene glycol, n is about 4.

* * * * *

UNITED STATES PATENT AND TRADEMARK OFFICE
CERTIFICATE OF CORRECTION

PATENT NO. : 5,750,122
DATED : March 12, 1998
INVENTOR(S) : Joel Franklin Evans et al.

It is certified that error appears in the above-identified patent and that said Letters Patent is hereby corrected as shown below:

Title page, item [56],

"Other Publications," line 2 "Panthenoln" should read --Panthenol--.
At column 1, line 46 "D-panthenol" should read --D-panthenyl--.
At column 2, line 38 "arc by weight" should read --are by weight--.
At column 2, line 59 "cleaners" should read --cleansers--.
At column 7, lines 60-61 "polymethylphenylsiloxan" should read --polymethylphenylsiloxane--.
At column 8, line 41 "crossliking" should read --crosslinking--.
At column 9, line 41 "biocidcs" should read --biocides--.
At column 11, line 5 "GIycol" should read --Glycol--.
At column 11, line 47 "PVPNA" should read --PVP/VA--.
At column 13, line 8 "Total Premix" should read --Total Premix--.

UNITED STATES PATENT AND TRADEMARK OFFICE
CERTIFICATE OF CORRECTION

PATENT NO. : 5,750,122

DATED : March 12, 1998

INVENTOR(S) : Joel Franklin Evans et al.

It is certified that error appears in the above-identified patent and that said Letters Patent is hereby corrected as shown below:

At column 13, line 48 "DisodiumEDTA" should read --Disodium EDTA--.

At column 16, line 14 "exceptDEA" should read --except DEA--.

At column 16, line 43 "composition useful" should read --composition is useful--.

At column 16, line 44 "to the skin" should read --to the skin.--.

At column 17, line 13 "Butylcarbarnate" should read --Butylcarbamate--.

Signed and Sealed this

Thirty-first Day of August, 1999

Q. TODD DICKINSON

*Attest:*

*Attesting Officer*   Acting Commissioner of Patents and Trademarks